(12) United States Patent
Ramminger et al.

(10) Patent No.: US 9,987,170 B2
(45) Date of Patent: Jun. 5, 2018

(54) WOUND DRESSING INCLUDING A BIOCELULOSE LAYER HAVING A BACTERIA-ADSORBING DESIGN

(75) Inventors: Ralf Ramminger, Bargteheide (DE); Hugh Andrews, Buchholz (DE); Patrick Schütz, Hamburg (DE)

(73) Assignee: BSN Medical GmbH, Hamburg (DE)

( * ) Notice: Subject to any disclaimer, the term of this patent is extended or adjusted under 35 U.S.C. 154(b) by 585 days.

(21) Appl. No.: 13/882,871

(22) PCT Filed: Nov. 1, 2011

(86) PCT No.: PCT/EP2011/069191
§ 371 (c)(1),
(2), (4) Date: Jul. 2, 2013

(87) PCT Pub. No.: WO2012/059488
PCT Pub. Date: May 10, 2012

(65) Prior Publication Data
US 2013/0296760 A1    Nov. 7, 2013

(30) Foreign Application Priority Data
Nov. 3, 2010    (DE) ........................ 10 2010 050 311

(51) Int. Cl.
*A61F 13/00*    (2006.01)
(52) U.S. Cl.
CPC .. *A61F 13/00063* (2013.01); *A61F 13/00012* (2013.01); *A61F 13/00029* (2013.01); *A61F 13/00046* (2013.01); *A61F 13/00987* (2013.01); *A61F 2013/0091* (2013.01); *A61F 2013/00157* (2013.01); *A61F 2013/00263* (2013.01);
(Continued)

(58) Field of Classification Search
CPC .......... A61F 13/00012; A61F 13/00029; A61F 13/00046; A61F 13/00063; A61F 13/00987; A61F 2013/00157; A61F 2013/00263; A61F 2013/00319; A61F 2013/00519; A61F 2013/00582; A61F 2013/00876; A61F 2013/0091
See application file for complete search history.

(56) References Cited

U.S. PATENT DOCUMENTS 4,588,400 A * 5/1986 Ring .................... A61L 15/28
424/447
4,655,758 A    4/1987 Ring et al.
(Continued)

FOREIGN PATENT DOCUMENTS

DE    19631421 A1    2/1998
DE    10135676 A1    2/2003
(Continued)

OTHER PUBLICATIONS

International Search Report for PCT/EP2011/069191 dated Oct. 2, 2012.

*Primary Examiner* — Kari Rodriquez
(74) *Attorney, Agent, or Firm* — Shumaker, Loop & Kendrick, LLP

(57) ABSTRACT

A wound dressing including at least one layer made of microbially produced cellulose formed into a biocellulose layer, wherein the wound dressing is configured to adsorb bacteria and wherein the thickness of the bio-cellulose layer is between 0.08 and 1.5 mm, as well as a method for producing such a wound dressing.

12 Claims, 1 Drawing Sheet

(52) U.S. Cl.
CPC ........... *A61F 2013/00319* (2013.01); *A61F 2013/00519* (2013.01); *A61F 2013/00582* (2013.01); *A61F 2013/00876* (2013.01)

(56) References Cited

U.S. PATENT DOCUMENTS

| | | | |
|---|---|---|---|
| 4,788,146 | A | 11/1988 | Ring et al. |
| 7,576,256 | B2 * | 8/2009 | Bjornberg ......... A61F 13/00042 602/48 |
| 2004/0028722 | A1 * | 2/2004 | Serafica et al. ............... 424/445 |
| 2006/0163149 | A1 | 7/2006 | Wadstrom et al. |
| 2008/0177214 | A1 | 7/2008 | Robertsson et al. |

FOREIGN PATENT DOCUMENTS

| | | |
|---|---|---|
| EP | 1356831 A1 | 10/2003 |
| EP | 1473047 A1 | 3/2004 |
| EP | 1438975 A1 | 11/2005 |
| WO | 86/02095 | 4/1986 |
| WO | 2004050986 A1 | 6/2004 |
| WO | 2005009276 A1 | 2/2005 |
| WO | 2006062470 A1 | 6/2006 |

\* cited by examiner

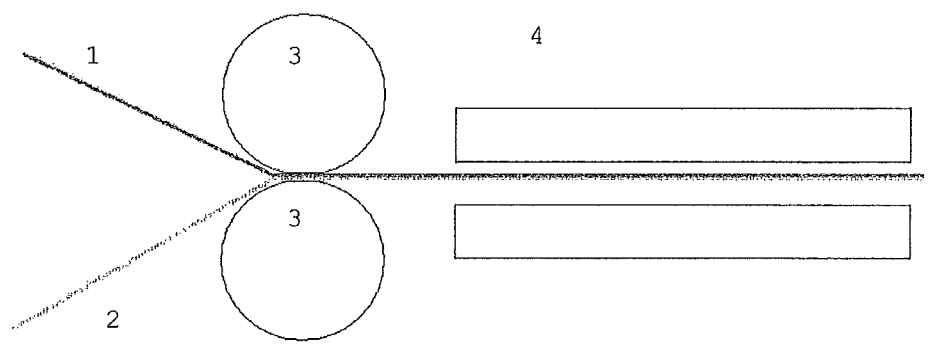

WOUND DRESSING INCLUDING A BIOCELULOSE LAYER HAVING A BACTERIA-ADSORBING DESIGN

TECHNICAL FIELD AND BACKGROUND OF THE INVENTION

The present invention relates to a wound dressing comprising at least one layer of microbially produced cellulose (biocellulose layer). The wound dressing is designed such that it adsorbs bacteria. The invention further relates to a method for producing such a wound dressing.

Wound dressings for healing burns, skin lesions or poorly healing wounds are known. Thus U.S. Pat. No. 4,588,400 A, U.S. Pat. No. 4,655,758 A and U.S. Pat. No. 4,788,146 A describe materials for such applications, which are produced on the basis of microbially produced cellulose. These documents also describe that the biocellulose layer can be impregnated with bacteriostatic agents such as silver nitrate or benzalkonium chloride. Methods for producing biocellulose are also described in WO 86/02095 A1 and WO 2004/050986 A. EP 1 356 831 A also describes the application of biocellulose in the treatment of wounds.

According to WO 2005/009276 A biocellulose can be provided with polyhexamethylene biguanide hydrochloride to impart antimicrobial activity. The corresponding wound dressings are intended to release moisture and are accordingly characterized by a very high water content and a correspondingly low cellulose content. In WO 2005/009276 A wound dressings are used specifically for chronic wounds. However, for burns, excessive moisture can be contraindicated.

EP 1 438 975 A discloses a moisture-releasing amorphous hydrogel based on microbial-derived cellulose for application to wounds.

In addition to the mentioned disadvantages of a high moisture (contraindicated for burns) the infection of the wound can be increased by such a gel.

The product Cuticell® Epigraft from BSN medical GmbH, Hamburg, Federal Republic of Germany, consists of a pure cellulose membrane which is formed by the microorganism *Acetobacter xylinum*. The product is transparent and thus allows the healing of the wound to be observed during treatment without the wound dressing having to be destroyed. Such biocellulose-based wound dressings are suitable for the treatment of split-skin graft donor sites, burns, skin cracks, wounds and skin lesions (such as skin abrasions, incised wounds and small surgical wounds). However, commercially available biocellulose-based wound dressings are thin and thus delicate during application. If applied incorrectly, contamination can easily occur. Thus infected wounds cannot be treated with biocellulose-based wound dressings. There is thus a requirement for wound dressings which can also be used for infected wounds as well as chronic wounds with exudate.

Bacteria-adsorbing compositions are also known. Thus EP 0 162 026 A describes that bacteria-adsorbing compositions can be used for treating external infections, which leads to a better removal of bacteria and other microorganisms. The compositions contain a hydrophilic material such as cotton which is rendered hydrophobic by treatment with for example dialkyl carbamoyl chloride.

Moreover WO 2006/062470 A discloses a wound dressing which has, on the side facing the wound, a hydrophobic layer which binds such microorganisms, above it an absorbent, hydrophilic layer, and a preferably transparent polyurethane layer as cover layer. The main task of such products is to adsorb bacteria, i.e. the field of use of such products is limited and they must always be combined with a further wound dressing. Such products are thus suitable particularly for short-term wound coverage.

DE 196 31 421 A also deals with hydrophobized carrier materials which can adsorb bacteria. The product Cutisorb® Sorbact® from BSN medical GmbH, Hamburg, Federal Republic of Germany, has for example a layer of hydrophobized acetate or cotton fabric.

DE 101 35 676 A discloses that (optionally microbially produced) cellulose can be doped with chitosan, hyaluronic acid or derivatives or mixtures thereof. The doped film is used, among other things, as physiological diaphragm, artificial bloodstream and/or a pump for infusion or dialysis. In such applications it is impossible for proteins to be absorbed, which is why the films according to DE 101 35 676 A do not adsorb bacteria.

BRIEF SUMMARY OF THE INVENTION

Thus the object of the present invention is to expand and improve the field of use of wound dressings, in particular biocellulose-based wound dressings. A special wound climate which is sealed off from external influences is to be created by the wound dressings according to the invention. The nanostructure of biocellulose is well suited for the adsorption of newly formed cells.

It has now surprising been shown that this object is achieved by a wound dressing which has at least one layer of microbially formed cellulose (called biocellulose layer below), wherein the wound dressing is designed such that bacteria are adsorbed. The biocellulose layer has a thickness of from 0.08 to 1.5 mm.

In a preferred embodiment the biocellulose layer is characterized by the following parameters:
- a thickness of from 0.10-0.25 mm,
- a water vapour transmission of more than 300 $g/m^2 \ast 24$ h, preferably of more than 500 $g/m^2 \ast 24$ h, in particular 1000-3000 $g/m^2 \ast 24$ h at 38° C., and/or
- a mass per unit area of 7 to 75 $g/m^2$, preferably 9-50 $g/m^2$, in particular 10-40 $g/m^2$, in particular 11-22 $g/m^2$.

Advantageously the biocellulose is a biocellulose produced according to a static method. This biocellulose has an advantageous three-dimensional multilayer structure. In contrast, biocellulose types which are produced in a stirred-tank bioreactor according to the teaching of U.S. Pat. No. 5,846,213 A1 are not preferred.

BRIEF DESCRIPTION OF THE DRAWINGS

FIG. 1 is a schematic diagram illustrating a method for producing the wound dressings according to one embodiment of the invention.

DETAILED DESCRIPTION OF THE INVENTION

According to a first embodiment of the invention the wound dressing is characterized in that the bacteria-adsorbing design consists of the biocellulose layer itself being designed hydrophobic. This hydrophobic design can be a treatment with dialkyl carbamoyl chloride and/or alkene ketene dimer as is known in the state of the art.

In preferred methods for the hydrophobic design of the biocellulose layer such a layer has a hydrophobic design when its biocellulose content is greater than approximately 5 wt.-%, preferably greater than 20 wt.-%, more preferably greater than 60 wt.-%, in particular preferably greater than 80 wt.-%, such as greater than 90 wt.-%, greater than 95 wt.-% or even greater than 97 wt.-%, such as for example 99 wt.-%.

In a second embodiment the bacteria-adsorbing design of the wound dressing consists of the wound dressing having, in addition to the biocellulose layer, at least one hydrophobic layer on the side of the biocellulose layer facing the wound.

This additional hydrophobic layer can contain cellulose acetate fabric, viscose fabric, cotton fabric or a mixed fabric, wherein hot-melt adhesive fibres are preferred as mixed fabric. Hydrophobic layers based on cellulose acetate fabric and cotton fabric, in particular cellulose acetate fabric, are particularly preferred. The hydrophobizing of the hydrophobic layer can consist of a treatment with dialkyl carbamoyl chloride and/or alkene ketene dimer. In a preferred embodiment the hydrophobic layer and the biocellulose layer are grown together in one production process. Alternatively it is possible that there is an adhesive layer between the hydrophobic layer and the biocellulose layer or that the two layers have been joined together by a lamination method.

If the base material used for producing the hydrophobic layer is naturally hydrophilic, as is the case for example with cellulose and viscose, this base material is treated with the help of a coating in order to produce the hydrophobic layer.

According to a third embodiment, in the case of the wound dressing according to the invention the biocellulose layer is designed hydrophobic and also a hydrophobic layer is present on the side of the biocellulose layer facing the wound.

There can also be a cover layer on the side of the biocellulose layer facing away from the wound. However, in a preferred embodiment there is no cover layer on the side of the biocellulose layer facing away from the wound. Instead, the wound is bandaged normally.

The production of biocellulose by bacteria is based on the excretion of nano-fine cellulose filaments by the bacteria. This process takes place in a controlled manner under specific climatic conditions in a nutrient solution. It is thus a biotechnical process. The bacteria gradually excrete so much cellulose that a gel cushion of biocellulose forms. By shaping or incorporation into the biocellulose gel cushion while it is still growing, the end-product can be influenced. For example it is thus possible to join together the additional hydrophobic layer and the biocellulose layer by ingrowth of the bacteria during the biotechnical production process.

The biocellulose can be grown such that it has open structures in order to promote healing of the wound by direct contact on the one hand and to transport the wound liquid of the infected wound into the wound dressing on the other, wherein the wound liquid with the infectious bacteria contained therein is adsorbed.

In all embodiments of the invention it is preferred that the wound dressing is provided with one or more antimicrobial substance(s) to render it antimicrobial. This design can consist of an impregnation of the biocellulose layer or of an impregnation of the biocellulose and hydrophobic layer. Alternatively the finished wound dressing can be designed antimicrobial in all layers contained therein.

The invention is suitable in particular for preventive application in split-skin harvesting or for burns, in particular when these wounds are already infected.

Split skin is suitable in particular for covering large areas, e.g. after burns, especially as the donor sites can regenerate quickly. The removal takes place usually on flat areas of skin, preferably on the thigh, back, bottom or stomach. In the harvesting of split skin, following subcutaneous injection of local anaesthetic, the uppermost epithelial layers are stripped with a scalpel or dermatome.

The invention also relates to a method for producing the wound dressings according to the invention. In a preferred method which is shown in FIG. 1, the biocellulose layer is provided in a moist state. The bacteria-adsorbing design is achieved by calendering. The wound dressing is oven-dried immediately after calendering. FIG. 1 shows
(1) the biocellulose layer in a moist state,
(2) the hydrophobic layer,
(3) the calendering rollers and
(4) the oven for drying.

In a first embodiment, on the wound side the wound dressing according to the invention comprises a (preferably open-meshed) acetate woven or cotton fabric with a mass per unit area of from 60 to 200 $g/m^2$, preferably 80 to 150 $g/m^2$, in particular 90 to 130 $g/m^2$, such as 110 $g/m^2$, provided with a microbially adhesive substance such as for example DAAC, joined to a top-side biocellulose layer with a mass per unit area of from 3 to 100 $g/m^2$, preferably 5 to 80 $g/m^2$, in particular 10 to 40 $g/m^2$.

In a further embodiment the wound dressing according to the invention comprises a cellulose-based nonwoven (viscose, cotton or as a mixture with non-cellulose fibres) with a mass per unit area of from 5 to 120 $g/m^2$, preferably 10 to 100 $g/m^2$, in particular 20 to 60 $g/m^2$, likewise provided with a microbially adhesive substance and a top-side biocellulose layer.

In a third embodiment the wound dressing according to the invention comprises the acetate fabric as described above which is surrounded by biocellulose, with the result that the total mass per unit area of the microbial cellulose, including the acetate fabric, is approximately 10 to 150 $g/m^2$, preferably 20 to 120 $g/m^2$, in particular 30 to 80 $g/m^2$.

The invention claimed is:

1. A wound dressing comprising at least one layer of microbially produced cellulose formed into a biocellulose layer, wherein
   (i) the wound dressing adsorbs bacteria,
   (ii) the biocellulose layer of the wound dressing has a thickness of from 0.08 to 1.5 mm, and
   (iii) at least one hydrophobic layer attached on a side of the biocellulose layer adapted to face a wound, wherein:
   the hydrophobic layer is treated with dialkyl carbamoyl chloride, alkene ketene dimer, or a combination thereof, and
   the biocellulose layer has a water vapour transmission rate of more than 300 $g/m^2$ per 24 h at 38° C.

2. The wound dressing according to claim 1, wherein the biocellulose layer has a thickness of from 0.10 to 0.25 mm.

3. The wound dressing according to claim 1, wherein the biocellulose layer has a mass per unit area of from 7 to 75 $g/m^2$.

4. The wound dressing according to claim 1, wherein the biocellulose layer is hydrophobic.

5. The wound dressing according to claim 1, wherein the hydrophobic layer is cellulose acetate fabric, viscose fabric, cotton fabric or a mixed fabric.

6. The wound dressing according to claim 5, wherein the mixed fabric comprises hot-melt adhesive fibres.

7. The wound dressing according to claim 1, wherein the hydrophobic layer and the biocellulose layer are joined together by ingrowth of bacteria during a biotechnical production process.

8. The wound dressing according to claim 1, wherein the biocellulose layer has a water vapour transmission rate of more than 500 g/m$^2$ per 24 h.

9. The wound dressing according to claim 1, wherein the biocellulose layer has a water vapour transmission rate of 1000 to 3000 g/m$^2$ per 24 h at 38° C.

10. The wound dressing according to claim 1, wherein the biocellulose layer has a mass per unit area of from 9 to 50 g/m$^2$.

11. The wound dressing according to claim 1, wherein the biocellulose layer has a mass per unit area of from 10 to 40 g/m$^2$.

12. The wound dressing according to claim 1, wherein the biocellulose layer has a mass per unit area of from 11 to 22 g/m$^2$.

* * * * *